(12) United States Patent
Koefer et al.

(10) Patent No.: US 6,716,221 B2
(45) Date of Patent: Apr. 6, 2004

(54) APPARATUS FOR SKIN PEELING

(75) Inventors: Doris Koefer, Klagenfurt (AT); Hannes Floessholzer, St. Paul (AT); Nikolaus Knoflacher, Klagenfurt (AT); Wolfgang Moser, Klagenfurt (AT)

(73) Assignee: Koninklijke Philips Electronics N.V., Eindhoven (NL)

( * ) Notice: Subject to any disclaimer, the term of this patent is extended or adjusted under 35 U.S.C. 154(b) by 249 days.

(21) Appl. No.: 10/105,524

(22) Filed: Mar. 25, 2002

(65) Prior Publication Data

US 2002/0143345 A1 Oct. 3, 2002

(30) Foreign Application Priority Data

Mar. 28, 2001 (GB) ............................. 01890100

(51) Int. Cl.$^7$ ................................................ A61B 17/50
(52) U.S. Cl. ..................................................... 606/131
(58) Field of Search ................................ 606/131, 132, 606/133; 604/289, 290

(56) References Cited

U.S. PATENT DOCUMENTS

| | | | |
|---|---|---|---|
| 2,917,056 A | 12/1959 | Dolan, Sr. | 132/75.8 |
| 3,169,536 A | 2/1965 | Caracciolo | |
| 5,112,341 A * | 5/1992 | Doley | 606/133 |
| 6,139,553 A | 10/2000 | Dotan | 606/131 |
| 6,471,712 B2 * | 10/2002 | Burres | 606/131 |
| 6,629,983 B1 * | 10/2003 | Ignon | 606/131 |

FOREIGN PATENT DOCUMENTS

DE 1948568 9/1969 ............ A61H/7/00

* cited by examiner

Primary Examiner—Kevin T. Truong

(57) ABSTRACT

An apparatus (1) for peeling the skin of a person has a drivable peeling tool (19), the drivable peeling tool (19) being mounted such that it can pivot about a pivot axis (21) within a specific pivoting angle range (β), said pivot axis (21) being perpendicular to the operating direction (20) of the apparatus (1) in a preferred design of the apparatus (1).

5 Claims, 2 Drawing Sheets

APPARATUS FOR SKIN PEELING

The invention relates to an apparatus for skin peeling having a housing which can be held in one hand and having a peeling tool which can be driven, said peeling tool can be moved over the skin of a person substantially parallel to an operating direction during operation of the apparatus and can be driven by drive means.

An apparatus with the design described in the first paragraph is disclosed, for example, in patent document U.S. Pat. No. 2,917,956 A. The known apparatus is a shaving apparatus in which a lower blade cooperating with an upper blade is normally driven to and fro parallel to a linear drive direction. However, it is also possible with this known shaving apparatus to achieve a peeling function instead of the shaving function, i.e. in that a peeling tool is mounted on a base part of the known shaving apparatus instead of the upper blade and the lower blade, it then being possible for the peeling tool to be driven to and fro parallel to the linear drive direction. If the peeling tool is connected to the base part of the shaving apparatus, the known shaving apparatus then in fact forms an apparatus for skin peeling. The peeling tool in this apparatus for skin peeling, and thus the peeling means connected to the peeling tool, can always be driven to and fro parallel to the linear drive direction only. Consequently, the peeling means interacts with the skin of a person practically always by its entire peeling surface during operation of this device, and so a relatively strong resistance is put in the way of the further movement of the peeling tool, and thus of the entire apparatus, along the skin of a person, something which, firstly, is felt to be unpleasant and which, secondly, may also lead to an uneven onward movement of the known apparatus and thus to an uneven skin peeling.

It is an object of the invention to avoid the problems set forth above in relation to a device for skin peeling and to create an improved device for skin peeling.

To achieve the above object in an apparatus for skin peeling in accordance with the invention, inventive features are provided such that an inventive apparatus for skin peeling can be defined as follows:

An apparatus for skin peeling having a housing which can be held in one hand, having a peeling tool which can be driven and which can be moved over the skin of a person parallel to an operating direction during operation of the apparatus, and having drive means for driving the peeling tool, the peeling tool being mounted such that it can pivot about a pivot axis and can be pivoted in a specific pivot angle range.

The result of the provision of the features in accordance with the invention is that the peeling tool, and thus the peeling means connected to the peeling tool, perform at least one slight pivoting movement in a structurally simple way during operation of the apparatus in accordance with the invention, as a result of which the apparatus in accordance with the invention can be moved with less resistance than the known apparatus, i.e. more easily over the skin of a person. Furthermore, it is advantageously achieved with the apparatus in accordance with the invention that the pivoting movement of the peeling tool produces brief impacts on the skin of a person which, on the one hand, intensify the peeling effect and additionally produce a massaging effect, which may be felt to be pleasant by a person using the apparatus in accordance with the invention, as was indeed found in trials that have been carried out.

In an apparatus in accordance with the invention, the pivot axis of the peeling tool may extend parallel to the operating direction. However, it has also proved to be very advantageous when the pivot axis is perpendicular to the operating direction. A particularly good peeling effect, and also a very good massaging effect, are achieved thereby.

It was found to be conducive to obtaining an advantageous structural design if the peeling tool has a substantially plate-shaped peeling means support to which a peeling means is connected, it having proved to be particularly advantageous if the peeling means is designed such that it can be removed from the peeling means support. This renders possible a simple structural design as well as the advantage that the peeling means can be easily and simply removed from the peeling means support in order, for example, to be cleaned or to be replaced by a new peeling means.

It was found to be particularly advantageous in an apparatus in accordance with the invention if in addition the features of claim 5 are provided. Such a solution offers the advantage that the entire peeling head can be easily exchanged. A further advantage of such a solution is that the peeling head may form part of an apparatus which has a base part on which the peeling head can be mounted, but on which it is also possible, however, to mount yet further treatment heads for carrying out personal hygiene and/or body treatments.

The above and further aspects of the invention will become apparent from the embodiment described below and will be explained with reference to this embodiment.

The invention will be described in more detail below with reference to an embodiment illustrated in the drawings, but the invention is not limited thereto.

Figure 1:
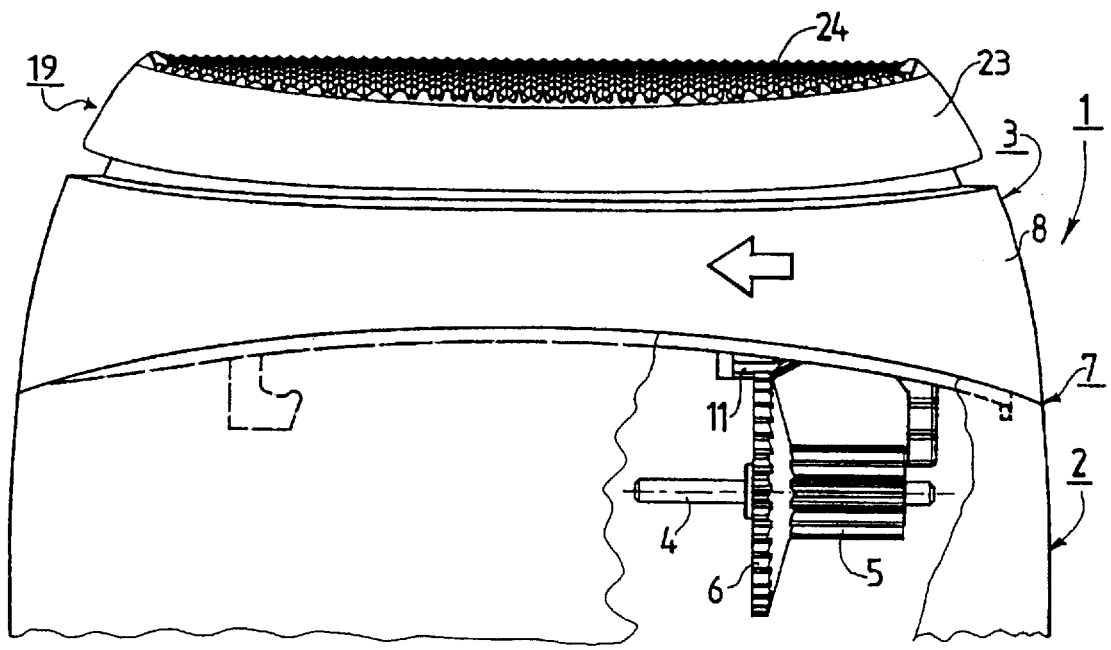
FIG. 1 shows part of an apparatus for skin peeling in accordance with an embodiment of the invention in front elevation, which apparatus has a peeling head.
Figure 2:
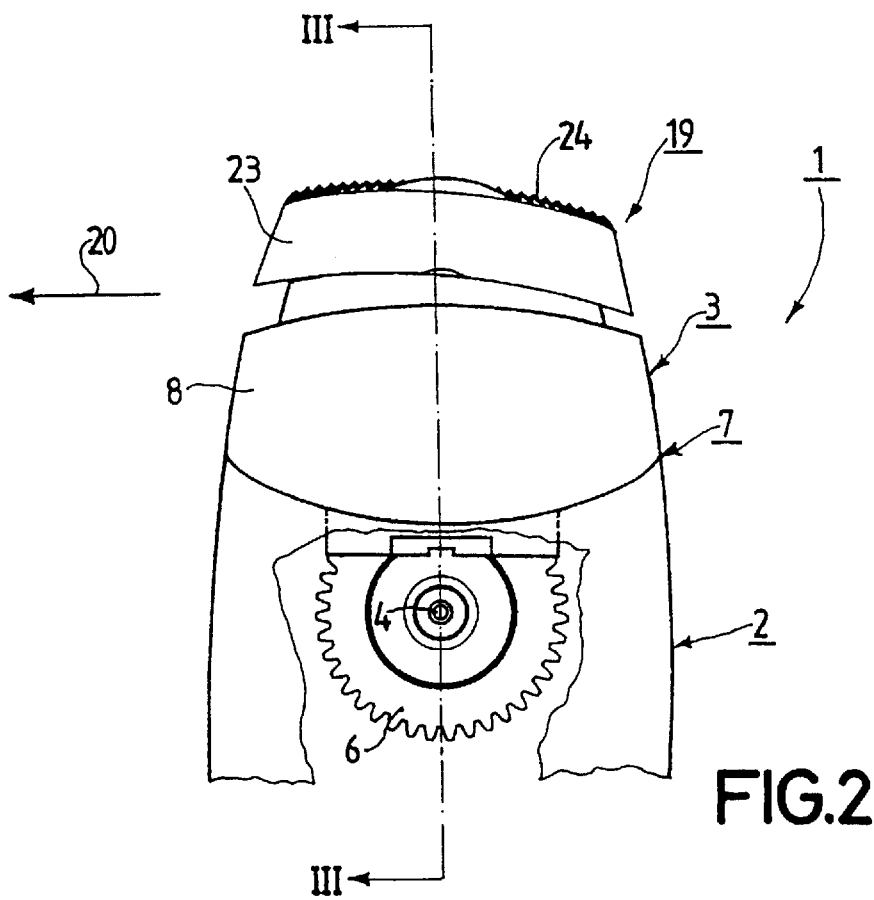
FIG. 2 shows the part of the apparatus of FIG. 1 in side elevation.

FIGS. 1 and 2 show an apparatus 1 for peeling human skin, by means of which apparatus 1 it is possible to peel off, and consequently remove, troublesome or undesired skin parts. The apparatus 1 comprises a base part 2 and a peeling head 3 detachably connected to the base part 2. The peeling head 3 can be mounted on the base part 2 and retained by retaining means (not illustrated). Included in the base part 2 are drive means which comprise a motor (not illustrated) and a gear unit (likewise not illustrated for the major part). All that is illustrated of the gear unit in FIGS. 1 to 4 is a pinion 5 that can be rotated about a spindle 4, and a toothed wheel 6 integrally joined to the pinion 5. With the peeling head 3 mounted on the base part 2, a substantially sealed housing 7 of the apparatus 1 is obtained.

Figure 3:
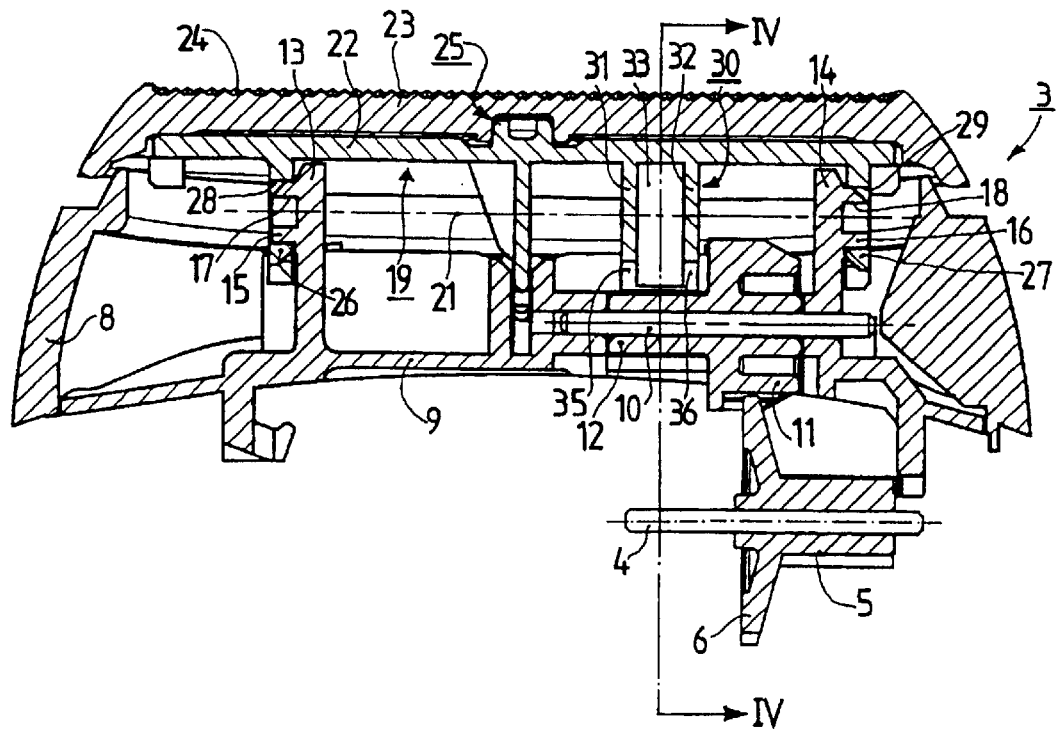
FIG. 3 is a cross-sectional view taken on the line III—III in FIG. 2 of the peeling head of the apparatus of FIGS. 1 and 2.
Figure 4:
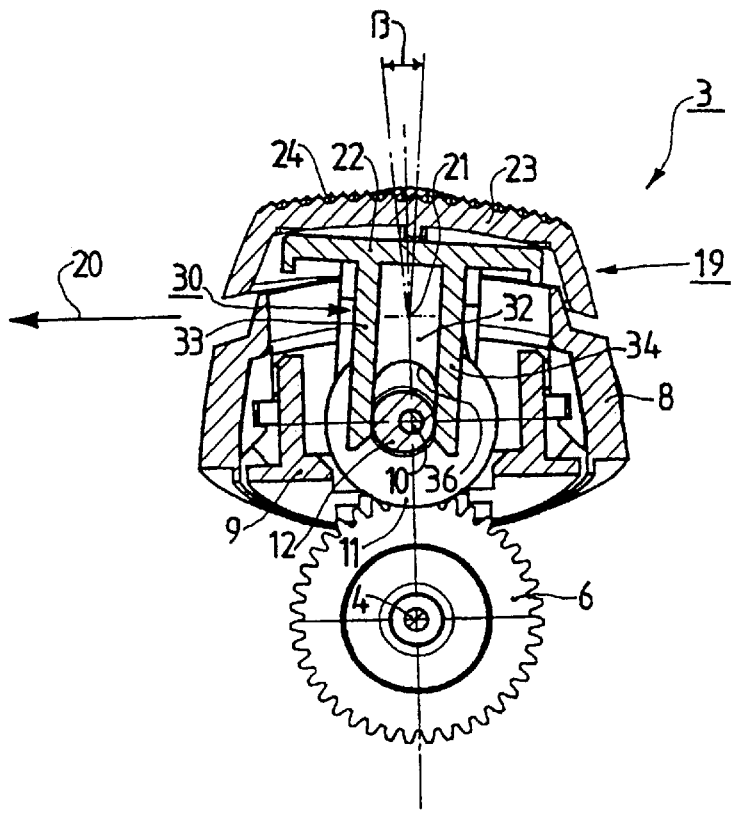
FIG. 4 is a cross-sectional view taken on the line IV—IV in FIG. 3 of the peeling head of FIG. 3.

As is readily in evidence from FIGS. 3 and 4, the peeling head 3 comprises a housing part 8, in which housing part 8a chassis unit 9 is held, the chassis unit 9 being connected to the housing part 8. A toothed wheel 11 is rotatably mounted in the chassis unit 9 by means of a further spindle 10, which toothed wheel 11 is integrally connected to an eccentric cylinder 12. The toothed wheel 1 can be disengaged from the toothed wheel 6 when the peeling head 3 is removed from the base part 2. Two bearing walls 13 and 14 project from the chassis unit 9. Projecting laterally from each of the two bearing walls 13 and 14 is a respective bearing cyclinder 15 and 16, one bore 17 or 18 being provided in each of the two bearing cylinders 15 and 16.

The peeling head 3 is equipped with a peeling tool 19. During operation of the apparatus 1 substantially parallel to an operating direction 20 as indicated with an arrow in FIGS. 2 and 4, the peeling tool 19 can be moved over the skin of a person, but it can also be moved in any other desired directions.

The peeling tool 19 is advantageously mounted such that it can pivot about a pivot axis 21 in the apparatus 1 shown in FIGS. 1 to 4. The peeling tool 19 has a substantially plate-shaped peeling means support 22 to which a peeling means 23 is connected. In the apparatus 1, the peeling means 23 comprises a synthetic-resin part which is provided with a peeling surface 24 on its free side, which peeling surface 24 is formed by a roughened surface realized during the injection-molding process. The peeling means 23 constructed as a synthetic-resin part is retained on the peeling means support 23 by means of a snap connection 25, as a result of which the peeling means 23 can be removed from the peeling means support 23 in a simple manner in order, for example, to be replaced by another peeling means or to be cleaned.

The peeling means support 22 has two bearing lugs 26 and 27 projecting from it. A bearing bore 28, 29 is provided for each of the two bearing lugs 26, 27. A bearing cylinder 15, 16 is held in each of the two bearing bores 28, 29, thus defining the pivot axis 21 for the peeling tool 23. In the present case, the pivot axis 21 extends perpendicularly to the operating direction 20.

A drive sleeve 30 of substantially rectangular cross section projects from the peeling means support 22, which drive sleeve 30 has two transverse walls 31 and 32 and two longitudinal walls 33 and 34. One substantially U-shaped passage 35, 36 is provided in each of the two transverse walls 31, 32, the eccentric cylinder 12 being guided through the two passages 35 and 36. The free ends of the two longitudinal walls 33 and 34 cooperate with the eccentric cylinder 12.

A rotating drive of the eccentric cylinder 12 will lead to a pivoting of the peeling tool 19 about the pivot axis 21, this pivoting being performed within a specific pivoting angle range $\beta$, as shown in FIG. 4.

The pivoting movement that can be imparted to the peeling tool 19 during operation of the apparatus 1 advantageously achieves a good peeling effect as well as a good massaging effect of the apparatus 1.

What is claimed is:

1. An apparatus (1) for skin peeling having a housing (7) which can be held in one hand, having a peeling tool (19) which can be driven and which can be moved over the skin of a person substantially parallel to an operating direction (20) during operation of the apparatus (1), and having drive means (5, 6, 11, 12, 30) for driving the peeling tool (19), the peeling tool (19) being mounted such that it can pivot about a pivot axis (21) and can be pivoted within a specific pivoting angle range ($\beta$).

2. An apparatus (1) as claimed in claim 1, wherein the pivot axis (21) is substantially perpendicular to the operating direction (20).

3. An apparatus (1) as claimed in claim 1, wherein the peeling tool (19) has a substantially plate-shaped peeling means support (22) to which a peeling means (23) is connected.

4. An apparatus (1) as claimed in claim 3, wherein the peeling means (23) is designed such that it can be removed from the peeling means support (22).

5. An apparatus (1) as claimed in claim 1, wherein the peeling tool (19) forms part of a peeling head (3) which is detachably connected to a base part (2) of the apparatus (1), and wherein the peeling head (3) is equipped with a drive part (11) which, upon detachment of the peeling head (3) from the base part (2) of the apparatus (1), can be disengaged from a drive part (6) accommodated in the base part (2) of the apparatus (1).

* * * * *